United States Patent
Duvick

(10) Patent No.: US 7,026,123 B1
(45) Date of Patent: Apr. 11, 2006

(54) UTR TAG ASSAY FOR GENE FUNCTION DISCOVERY

(75) Inventor: Jon Duvick, Des Moines, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 264 days.

(21) Appl. No.: 10/229,608

(22) Filed: Aug. 28, 2002

Related U.S. Application Data

(60) Provisional application No. 60/315,942, filed on Aug. 29, 2001.

(51) Int. Cl.
  C12Q 1/68 (2006.01)
  C12P 19/34 (2006.01)
  C12P 21/06 (2006.01)
  C07H 19/00 (2006.01)

(52) U.S. Cl. .................. 435/6; 435/69.1; 435/91.2; 536/22.1

(58) Field of Classification Search ............ 435/6, 435/69.1, 91.21; 536/24.33, 22.1
See application file for complete search history.

(56) References Cited

U.S. PATENT DOCUMENTS

| | | |
|---|---|---|
| 5,604,097 A | 2/1997 | Brenner |
| 5,846,719 A | 12/1998 | Brenner et al. |
| 5,866,330 A | 2/1999 | Kinzler et al. |
| 5,876,931 A | 3/1999 | Holden |
| 5,981,730 A | 11/1999 | Ausubel et al. |
| 6,013,445 A | 1/2000 | Albrecht et al. |
| 6,150,516 A | 11/2000 | Brenner et al. |
| 6,172,214 B1 | 1/2001 | Brenner |
| 6,172,218 B1 | 1/2001 | Brenner |
| 6,228,589 B1 | 5/2001 | Brenner |
| 6,235,475 B1 | 5/2001 | Brenner et al. |
| 6,352,828 B1 | 3/2002 | Brenner |
| 6,835,540 B1 | 12/2004 | Broun |
| 2002/0106673 A1 | 8/2002 | Drmanac et al. |
| 2002/0155540 A1* | 10/2002 | Padidam ............ 435/69.1 |

FOREIGN PATENT DOCUMENTS

| | | |
|---|---|---|
| EP | 0 973 943 B1 | 9/2002 |
| WO | WO 96/17951 | 6/1996 |
| WO | WO 96/41011 | 12/1996 |
| WO | WO 97/14812 | 4/1997 |
| WO | WO 98/07886 | 2/1998 |
| WO | WO 00/20639 | 4/2000 |
| WO | WO 00/79264 A1 | 12/2000 |
| WO | WO 01/61346 A2 | 8/2001 |

OTHER PUBLICATIONS

Luehrsen K, et al. Insertion of non-intron sequence into maize introns interferes with splicing. Nucleic Acids Res., vol. 20, No. 19, pp. 5181-5187, 1992.*

Cannons, et al., The stability of the *Chlorella* nitrate reductase mRNA is determined by the secondary structure of the 5'-UTR: Implications for posttranscriptional regulation of nitrate reductase, Planta, 2002, 214: 488-491.

Cok, et al., The 3'-Untranslated Region of Murine Cyclooxygenase-2 Contains Multiple Regulatory Elements That Alter Message Stability and Translational Efficiency, J. Biol. Chem., 2001, 276(25):23179-23185.

Smolke, et al., Effects of transcription induction homogeneity and transcript stability on expression of two genes in a constructed operon, Appl. Microbiol. Biot, 2001, 57: 689-696.

Oliphant, et al., Cloning of random-sequence oligodeoxynucleotides, 1986, Gene, 44: 177-183.

Bendahmane, A., "*Agrobacterium* Transient Expression System as a Tool for the Isolation of Disease Resistance Genes: Application to the Rx2 Locus in Potato," *The Plant Journal*, 2000, pp. 73-81, vol. 21(1).

Bruce, W., et al., "Expression Profiling of the Maize Flavonoid Pathway Genes Controlled by Estradiol-Inducible Transcription Factors CRC and P," *The Plant Cell*, 2000, pp. 65-79, vol. 12.

Goff, et al., "Transactivation of Anthocyanin Biosynthetic Genes Following Transfer of B Regulatory Genes Into Maize Tissues," *The EMBO Journal*, 1990, pp. 2517-2522, vol. 9(8).

(Continued)

*Primary Examiner*—Jeffrey Fredman
*Assistant Examiner*—Suryaprabha Chunduru
(74) *Attorney, Agent, or Firm*—Alston & Bird LLP

(57) ABSTRACT

The methods of the invention provide a means for rapid analysis of gene function in a variety of systems. The invention allows screening of large libraries of nucleotide sequences for involvement in physiological pathways of interest. The methods of the invention also provide an efficient means of identifying and isolating nucleotide sequences that modulate a physiological pathway of interest from a population of nucleotide sequences.

67 Claims, 4 Drawing Sheets

OTHER PUBLICATIONS

Hattori, T., et al., "Regulation of the *Osem* Gene by Abscisic Acid and the Transcriptional Activator VP1: Analysis of Cis-acting Promoter Elements Required for Regulation by Abscisic Acid and VP1," *The Plant Journal*, 1995, pp. 913-925, vol. 7(6).

Nantel, A., and R.S. Quatrano, "Characterization of Three Rice Basic/Leucine Zipper Factors, Including Two Inhibitors of EmBP-1 DNA Binding Activity," *The Journal of Biological Chemistry*, 1996, pp. 31296-31305, vol. 271(49).

Sessa, G., et al., "A Transient Assay for Rapid Functional Analysis of Transcription Factors in Arabidopsis," *Plant Molecular Biology Reporter*, 1998, pp. 191-197, vol. 16.

Yang, Y., et al., "In vivo Analysis of Plant Promoters and Transcription Factors by Agroinfiltration of Tobacco Leaves," *The Plant Journal*, 2000, pp. 543-551, vol. 22(6).

* cited by examiner

US 7,026,123 B1

UTR TAG ASSAY FOR GENE FUNCTION DISCOVERY

FIELD OF THE INVENTION

The present invention relates to the field of molecular biology, more particularly to the characterization of gene function in host cells.

BACKGROUND OF THE INVENTION

A variety of genetic and biochemical studies have proved that virtually any biological process (i.e., cell behaviors and the like) can be broken down into components. This reductionist approach to biological inquiry seeks to understand the greater part of life's complexity in the relatively simple chemical terms of molecules and molecular interactions. In the middle part of the twentieth century, several scientists showed that metabolism can be understood as a series of enzymes that act sequentially to convert precursor compounds into final metabolic products. This insight gave rise to the notion of genetic or biochemical pathways that control cellular processes. More complicated cellular behaviors such as differentiation have recently been defined in terms of genetic programs and pathways. Even disease processes can be thought of in such terms. For example, the hypersensitive response of plants is a pathway characterized by cell collapse, cell dying, the deposition of callose, the physical thickening of cell walls by lignification, and the synthesis of various antibiotic small molecules and proteins. An effective strategy to study the hypersensitive response involves the elucidation of pathogenesis-response pathways.

Genes regulate some of the most commercially, agriculturally, and medically important processes in biology. However, determining which genes function in what pathway is a complex process. There are few methods available to screen large numbers of genes or promoters in plant cells for their effect on expression in a physiological pathway of interest. Co-bombardment methods that allow read-out of a marker-linked promoter based on the action of another gene in trans (See, U.S. Pat. No. 5,981,730, Ausubel et al (1995) *Current Protocols in Molecular Biology*, Greene Publishing and Wiley-Interscience, New York) are not amenable to high throughput analysis. Other methods that use Tobacco Mosaic Virus to screen for cDNA inserts that give a local lesion response in a normally non-necrotic mutant are not suitable for the detection of positive phenotypes. Methods such as the yeast two hybrid system only allow identification of genes that encode polypeptides that directly interact with a known polypeptide. Many of the currently available methods for identifying genes that function in a particular pathway require cumbersome analysis of complex phenotypes. Consequently, in many of the available methods, identification of the genes that function in the pathway of interest is neither rapid nor efficient. Methods that are capable of identifying the underlying genes that regulate important biological pathways, such as the plant pathogenesis response or mammalian tumor progression, would thus be of great value.

Clearly a general method of functional genetic analysis is needed. The method should be simple, rapid, allow high throughput screening, and permit identification of components of genetic pathways that regulate traits of interest. The method should not require an understanding of the detailed basis of a particular phenotype or the mechanisms that underlie specific cellular behaviors. The method should be generally applicable to a great variety of cells, including cells cultured from somatic tissues of multicellular organisms, and it should allow rapid isolation of the nucleotide sequences that function in the pathway of interest.

SUMMARY OF THE INVENTION

The present invention provides methods and compositions for the identification of nucleotide sequences that modulate, either directly or indirectly, the activity of a transcriptional regulatory region (TRR), particularly a TRR specific to a physiological pathway of interest. The method identifies nucleotide sequences that directly modulate the TRR by directly interacting with it. Alternatively, the methods allow for the identification of nucleotide sequences that indirectly modulate a TRR by influencing proteins or other molecules that interact with the TRR. The modulation of a TRR that is specific to a physiological pathway of interest by a nucleotide sequence of interest indicates that the nucleotide sequence functions in that physiological pathway of interest.

One method of the invention includes stably incorporating into a host cell a plasmid having at least a first and a second DNA construct. The first DNA construct includes the following components: a TRR, a reporter sequence, one or more non-redundant U-tags, and an mRNA stabilizing sequence. The second DNA construct includes a promoter active in the host cell operably linked to a nucleotide sequence of interest. The host cells are subsequently screened for an alteration in U-tag expression levels.

Similarly, a library of plasmids, each having one or more non-redundant U-tags, may be generated. Each plasmid in the library includes a first and a second DNA construct as previously described. The library is incorporated into a population of host cells and screened for an alteration in the expression levels of each U-tag.

Using the plasmid library, the present invention enables the assaying of large numbers of nucleotide sequences for involvement in a particular physiological pathway of interest, as evidenced by modulation of the activity of a TRR specific to a particular physiological pathway of interest. Such pathways include, but are not limited to, pathogen resistance pathways, tissue developmental pathways, metabolic pathways, apoptotic pathways, and pathways involved in presentation of a disease.

Methods of screening for an alteration in U-tag expression levels may be selected from the group consisting of, but not limited to, hybridization to a complementary U-tag array, sequence probe concatamer methods, or solid phase capture systems. The method of the present invention further comprises isolating from the library at least one plasmid having one or more non-redundant U-tags with an altered expression level.

Another method of the present invention comprises a method for identifying TRRs that are modulated by an agent. The agent used in the methods of the invention includes, but is not limited to, a pathogen, a polypeptide, a nucleotide sequence, or a small molecule. This method allows identification of TRRs such as promoters or enhancers that are responsive to an agent known to regulate a physiological pathway of interest. A response by the TRR to the agent indicates that the TRR is modulated in the physiological pathway of interest.

The method comprises using the library of plasmids as previously described, which have been incorporated into a host cell population. The host cells are contacted with an agent that regulates a physiological pathway of interest. The mRNA from the host cells is screened for an alteration in expression levels of each U-tag, enabling the isolation of at least one plasmid from the library with an altered U-tag expression level.

Compositions of the invention include a library of plasmids that is characterized as a collection of plasmids each having one or more non-redundant U-tags. Each plasmid in the library comprises a first DNA construct and a second DNA construct. The first DNA construct includes the following components: a multiple cloning site; a reporter sequence; one or more U-tags; and an mRNA stabilizing sequence. The second DNA construct includes a promoter active in the host cell operably linked to a multiple cloning site. Further compositions of the invention include libraries of plasmids used in the methods of the present invention and kits for performing the methods of the invention.

An additional method of the present invention comprises a method for identifying nucleotide sequences of interest that modulate the activity of a TRR, where the size and DNA content of the nucleotide sequences of interest are very similar, such as nucleotide sequences derived from DNA shuffling. The close juxtaposition of the U-tag or tags and the nucleotide sequences of interest increases the efficiency of the recovery of "hits" using U-tag primed PCR.

The method comprises generating a library of plasmids similar to those already described, wherein each plasmid in the library comprises only a first DNA construct having the following components: a TRR, one or more U-tags, a nucleotide sequence of interest, and an mRNA stabilizing sequence. The library is incorporated into a population of host cells. The mRNA from the host cells is screened for an alteration in expression levels of each U-tag. The method further comprises isolating at least one plasmid from the library with an altered U-tag expression pattern. In this method, the TRR comprises a weak constitutive promoter that allows low levels of expression. The nucleotide sequences of interest serve as both activator and reporter; the nucleotide sequence activates expression of itself and thus increases the signal frequency of the linked U-tag or tags.

Further compositions of the invention include a library of plasmids that is a collection of plasmids each having one or more non-redundant U-tags. Each plasmid in the library comprises a first DNA construct. The first DNA construct comprises the following components: a multiple cloning site; a reporter sequence; one or more U-tags; and an mRNA stabilizing sequence. Further compositions of the invention include libraries of plasmids used in the methods of the present invention and kits for performing the methods of the invention.

The methods and compositions of the invention may be used in any system for which suitable culture and transformation methods exist or are developed as the art advances. An embodiment of invention comprises host cells that are selected from the group consisting of, but not limited to, plant cells (dicotyledonous and monocotyledonous), animal cells (mammalian, reptilian, amphibian, piscine, arthropodan), fungal cells and bacterial cells. The host cells of the invention may survive in culture or in whole organism systems. In one embodiment of the invention the plant cells are selected from the group consisting of maize, wheat, sorghum, rice, barley, soybean, alfalfa, sunflower, Brassica, and tomato.

DETAILED DESCRIPTION OF THE INVENTION

Figure 1:
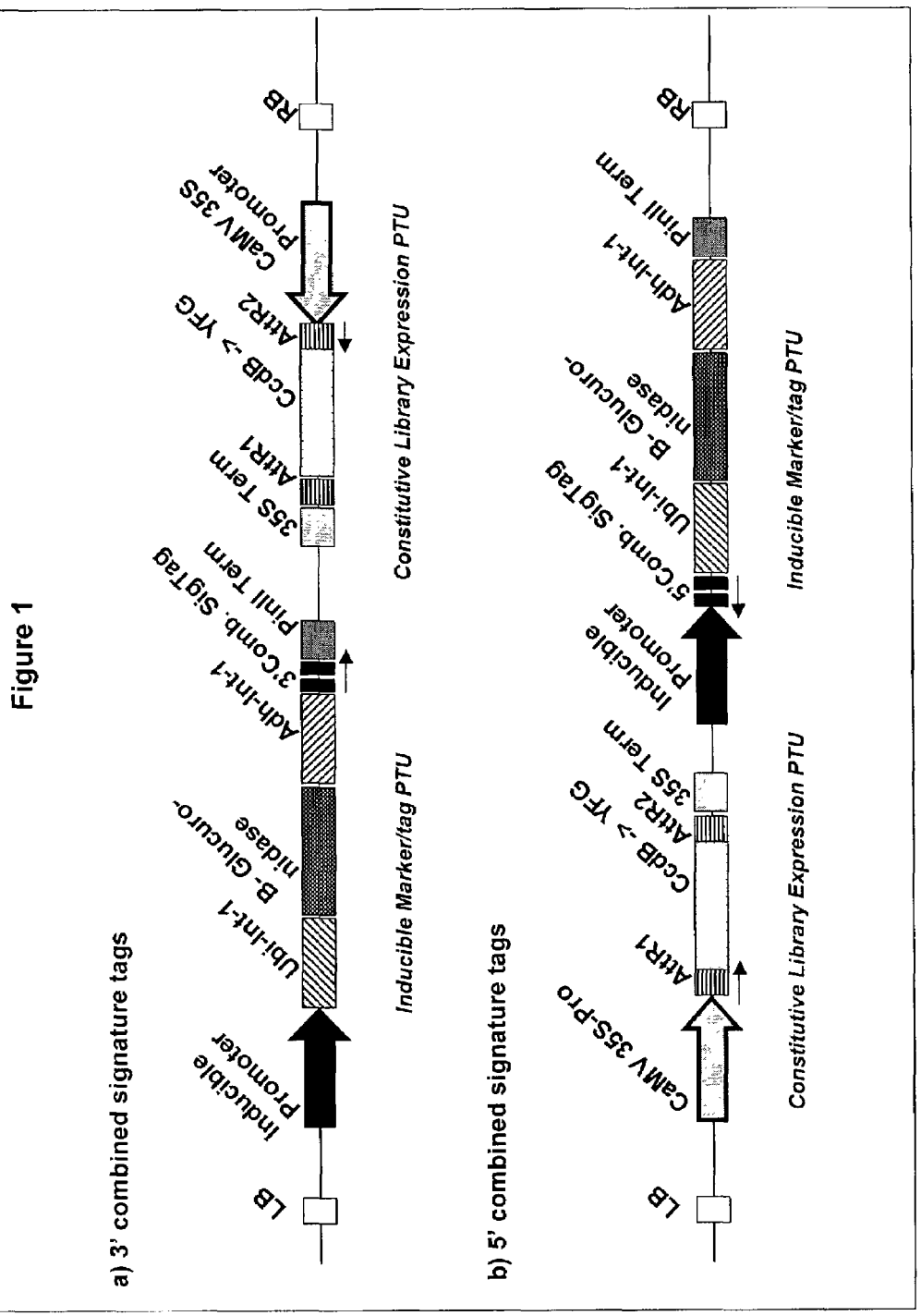
FIG. 1 represents a construct design for a dual plant transcription unit (PTU) with a combined U-tag at either the 5' or 3' UTR location. The small arrows in the figure represent possible gene rescue primer locations. The abbreviations LB and RB refer, respectively, to left and right T-DNA border.
Figure 2:
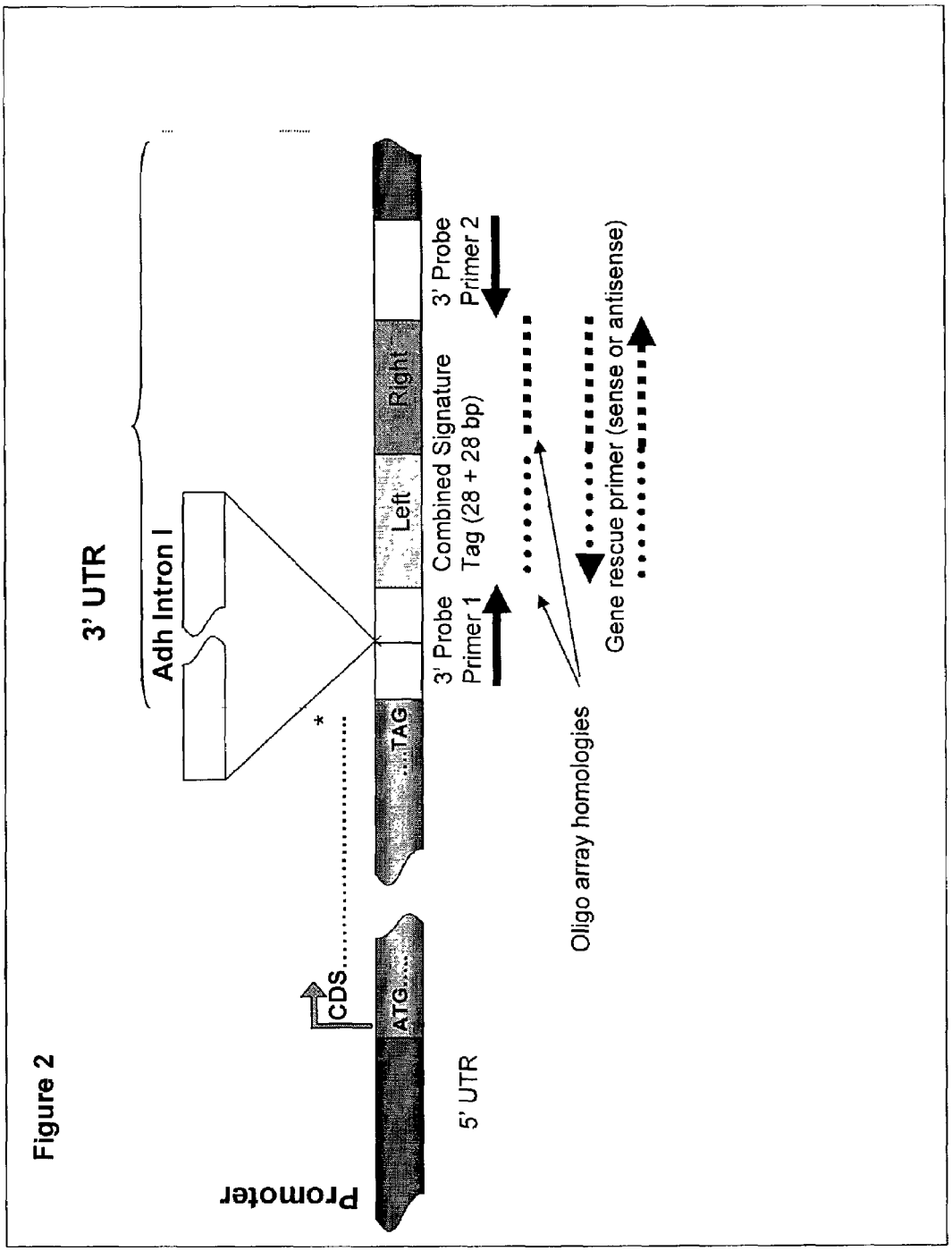
FIG. 2 depicts a diagram of a combined U-tag strategy. The design includes dual U-tags, with both primers in the 3' (or 5') UTR of a coding sequence, flanked by PCR primers and driven by an inducible promoter. An intron interrupts one flanking primer to ensure that only cDNA, not genomic DNA, is amplified for probing. To rescue positives, PCR primers based on combined left and right tags are used with a common second primer to specifically amplify the coding region of a positive clone from cDNA or genomic DNA. The gene to be rescued can be either part of the inducible U-tag ORF or in a second ORF driven by a constitutive promoter.

The present invention provides a method for the evaluation of the functional role of large numbers of candidate clones in a physiological pathway of interest. Further compositions of the invention include kits that allow one to rapidly evaluate the functional role of large numbers of candidate clones in a physiological pathway of interest. The invention further provides a method for identification of mutant forms of a nucleotide sequence that exhibit altered behavior with respect to the physiological pathway of interest. The invention allows evaluation of direct and indirect effects of the candidate clones on the physiological pathway of interest in the context of the native cell.

By "directly modulates the activity of a transcriptional regulatory region" it is intended that the nucleotide sequence of interest is transcribed into an RNA molecule that modulates the activity of the transcriptional regulatory region or that the nucleotide sequence of interest encodes a peptide, polypeptide, or protein that binds the transcriptional regulatory region. An RNA molecule may modulate the activity of the transcriptional regulatory region through a variety of mechanisms including, but not limited to, antisense suppression, hairpin formation, or competing with the transcriptional regulatory region for interacting agents. A peptide, polypeptide, or protein that binds the transcriptional regulatory region may increase or decrease the activity of the transcriptional regulatory region.

By "indirectly modulates the activity of a transcriptional regulatory region" it is intended that the nucleotide sequence of interest encodes a peptide, polypeptide, or protein that interacts with a cellular component, such as, a peptide, polypeptide, protein, RNA, or small molecule that then modulates the activity of the transcriptional regulatory region. The peptide, polypeptide, or protein encoded by the nucleotide sequence of interest may produce, alter, or modify a cellular component that then modulates the activity of the transcriptional regulatory region. The peptide, polypeptide, or protein encoded by the nucleotide sequence of interest may interact with a cellular component of a signal cascade that results in modulation of the activity of the transcriptional regulatory region. The peptide, polypeptide, or protein encoded by the nucleotide sequence of interest may interact with a cellular component that interacts with a component or a sequence of cellular components that results in modulation of the activity of the transcriptional regulatory region. The peptide, polypeptide, or protein encoded by the nucleotide sequence of interest may interact with a component of a physiological pathway, including but not limited to, a component 1, 2, 3, 4, 5, 6, 7, 8, 9, 10, 11, 12, 15, or 20 molecules removed from the cellular component that directly interacts with the transcriptional regulatory region.

The method comprises generating a library of unique plasmids that can be stably transformed into a host cell, particularly a plant cell. As described below, the plasmids that constitute the library contain one or more non-redundant U-tag sequences and a candidate sequence. A U-tag sequence confers an identifying marker on each plasmid in the library. The U-tag allows rapid identification and retrieval of plasmids that contain candidate sequences that function in a physiological pathway of interest. The method allows high throughput functional analysis of large numbers of uncharacterized candidate clones in both plant and animal cells.

By "U-tag" a short, random nucleotide sequence such as an oligonucleotide signature tag (OST) or an intron interrupted signature probe in the untranslated region of a reporter sequence is intended. For purposes of the present invention, a U-tag is an untranslated region tag when the U-tag is inserted into an untranslated region. In addition, a U-tag can in fact be a signature tag when it is inserted into a coding region. A single U-tag can be inserted in either the 5' untranslated region or the 3' untranslated region of the reporter sequence. Alternatively, two U-tags can both be inserted in either the 5' untranslated region or the 3' untranslated region of the reporter sequence, or two U-tags can be inserted such that one tag is located in the 5' untranslated region and the second tag is located in the 3' untranslated region. One of skill in the art will recognize that the U-tag oligonucleotide can be designed in various ways and can be inserted into the DNA construct in a variety of positions. The length of the U-tag can vary depending on the desired complexity of the U-tag population ranging between about 10–100 nucleotides, about 10–80 nucleotides, about 15–60 nucleotides, or about 15–50 nucleotides.

U-tags could be designed as an in-frame coding region, which would result in a random amino- or carboxy-terminal fusion with the open reading frame. Ideally an amino-terminal tag would be designed with a methionine (ATG) start and would be required to avoid stop codons. Such constraints need not apply to a carboxy-terminal tag. Numerous fusion proteins retain their functionality. It is expected that a U-tag of 24 to 60 base pairs would not perturb protein function.

A U-tag could also be designed into an intron sequence that occurs anywhere within a transcript. The U-tag is designed in such a way that the consensus sequences are not disturbed. For example, these sequences can be designed with a splice donor, lariat site or splice acceptor that confers intron spliceability. See, Genes VII, published by Oxford University Press (2000). In this design, the spliced-out intron RNA would be detected at a level proportional to the transcription rate. Recent data from mammalian cells indicates that intron RNAs, after splicing, persist in the cell with reasonable half-lives, contrary to what was previously thought. See, Clement et al. (2001) J. Biol. Chem. 276: 16919–30. Other sequences contributing to RNA stability may be added to the intron in order to increase half-life. Examples of such stabilizing sequences include a poly-A tract, which stabilizes mRNAs (see Genes VII, supra), viral RNA sequences involved in stabilization of single-stranded RNA (see Miller et al. (1998) J. Mol. Biol. 284: 591), or other RNA stabilizing motifs (see Janeau et al. (1999) RNA 5: 1119–29). An advantage of intron localization of tags would be that variations in mRNA stability of coding regions would not be a factor in accumulation of tag RNA. A disadvantage, however, would be that intron splice junctions could not be used to provide cDNA-specificity at the probe amplification step, since the entire amplicon will need to be contained within the intron region.

A further method for designing U-tags allows the development of a population of U-tags with equivalent melting temperatures among the members of the population and maximizes the differences between the U-tags to increase specificity during hybridization. The U-tag population will contain about 30%–70% GC content, about 40%–60% GC content, or about 45%–55% GC content. The U-tag oligonucleotides can be assembled from blocks of 3 to 6 deoxynucleotides of G, A, T, and C (or a subset thereof) in various combinations, such that each block contains no more than one duplicated nucleotide at any position. Blocks are strung together to generate combinations of blocks. In this way, even a one-block difference between two sequences will always result in a 3 base pair difference between U-tags. The blocks could be synthesized in two unique sets having an overlapping constant domain that allows them to be ligated to each other in random combination during cloning.

Additional methods for generating random or diverse oligonucleotides are known to one of skill in the art (Ausubel et al. (1995) *Current Protocols in Molecular Biology*, Greene Publishing and Wiley-Interscience, New York and WO 00/20639; both of which are herein incorporated by reference). Such methods include the use of degenerate oligodeoxynucleotides with palindromic ends that can self-prime in a Klenow fill-in reaction, to generate a clonable double-stranded fragment. This method generates a highly diverse tag population (Oliphant et al. (1986) *Gene* 44:177, herein incorporated by reference).

Construction of the U-tag population will be optimized to minimize the frequency of multiple occurrences of the same sequences. Each U-tag will occur rarely in the total population of U-tags, more preferably, each U-tag occurs once in the U-tag population. The methods of the invention allow the complexity of the U-tag population to be limited to a reasonable level and still allow a good probability of detecting a rare "hit" or active clone. Low complexity is desirable because of the need to detect and quantify expression of all the U-tags. The complexity of the U-tag population will be in the range of about 1 to $5 \times 10^3$ to 1 to $5 \times 10^7$, about 1 to $5 \times 10^4$ to 1 to $5 \times 10^6$, or about 1 to $5 \times 10^4$ to 1 to $5 \times 10^5$. A signature population that is only moderately complex ($10^5$ members) will result in a given signature being linked to more than one library member; however, if the ratio of sample size to U-tag complexity is kept low enough (e.g. less than 0.5), there is a good probability that a rare "hit" is likely to have a non-redundant U-tag with respect to the portion of the library sampled.

Redundancy is defined as the occurrence of two or more distinct library clones in a sample pool that share the same U-tag. The most desirable redundancy class for an efficient U-tag screen is one or two, since this provides the most straightforward way to detect and identify "hit" candidate clones. As used herein, by "non-redundant U-tag" it is intended that no more than about 20% of the U-tag sequences occur more than once in the library, no more than about 10% of the U-tag sequences occur more than once in the library, no more than about 5% of the U-tag sequences occur more than once in the library, that no more than about 1% of the U-tag sequences occur more than once in the library, or that no more than about 0.5% of the U-tag sequences occur more than once in the library. The non-redundant identifier or U-tag allows rapid identification of plasmids containing the U-tag of a "hit" candidate clone using a variety of methods.

The use of two U-tags in the DNA construct will further reduce the potential for redundancy by generating extremely high variability in the plasmid library. The combined U-tag population, which is equal to the square of the individual U-tag population size, is large enough that each clone being sampled has a very high likelihood of being unique in the combination of U-tags. For example, if two populations of U-tags each contain 1000 members, the total number of unique signatures possible in a construct containing one U-tag from each of the two populations is $1000^2$, or 1 million. It follows that if 10,000 library clones were selected for a given experiment, each individual clone would have a very high probability of being unique in any given sample.

A "hit" clone is a nucleotide sequence of interest that modulates, directly or indirectly, the activity of a transcriptional regulatory region. By "modulates the activity" of a transcriptional regulatory region an increase or decrease in the efficacy or efficiency of a transcriptional regulatory region as measured by a 0.5%, 1%, 5%, 10%, 20%, 30%, 40%, 50%, 60%, 70%, 80%, 90%, or 100% change in transcript levels of a reporter sequence controlled by the transcriptional regulatory region is intended. The reporter sequence includes the U-tag or tags. Thus, a "hit" clone will be characterized by an alteration in the expression level of the associated U-tag or tags. In one embodiment, the relative expression levels of each U-tag with and without a nucleotide sequence of interest in the second DNA construct are compared. In another embodiment, the relative expression of each U-tag with and without a nucleotide sequence of interest in the first DNA construct are compared. In extreme cases, the nucleotide sequence of interest leads to cell death and a concomitant decrease or loss of the reporter sequence.

Identification of the "hit" clones relies on amplification of the U-tag population from the host cells in a fashion that preserves relative signature abundance sufficient to allow outliers, which are "hit" clones that modulate the activity of the transcriptional regulatory region to be selected, either by low abundance, high abundance, or absence of the U-tag from the signature pool. Any method available in the art can be used to identify "hit" clones. Since the field of high throughput DNA detection and discrimination is growing rapidly, the method of DNA detection and discrimination is not critical to the instant invention. Various methods of detecting and identifying "hit" clones are currently known and any method, which provides for effective DNA detection and discrimination may be employed.

One method for DNA detection employs the use of oligonucleotide arrays in which complementary oligonucleotide signatures used to tag the library are arrayed on a microchip and hybridized with labeled cDNA amplified from the U-tag region of mRNA transcripts. Such an oligonucleotide array will be referred to herein as a "complementary U-tag array." Another method for DNA detection is sequencing probe concatamers such as those used in Serial Analysis of Gene Expression (SAGE)(U.S. Pat. No. 5,866, 330 herein incorporated by reference). Additional methods include the use of solid-phase capture systems combined with parallel sequencing that allow U-tags to be captured, arrayed, and sequenced in large numbers. Another method for DNA detection includes quantitative PCR using primers based on the U-tag sequences in combination with a detection system that allows amplified product to be detected above a background of non-amplified material. Commercial kits and equipment are available (e.g. Taqman) to one of skill in the art to accomplish semi-quantitative PCR detection of low-level sequences at high throughput (for example, spin blotting used for polymorphism detection and TUSC). Yet another method of DNA detection includes hybridization to colony blots in which the amplified mRNA U-tag population is hybridized to the original input library DNA in array format generated by lysis on membranes of replica-plated bacterial colonies on a grid array under conditions that allow differences in U-tag frequency to be detected. An additional method is mass spectrometry of amplified probe fragments to distinguish molecular weights and/or fragmentation patterns (e.g. Deforce et al. (2000) *Adv. Chromatogr.* 40:539).

The preparation of a probe or sequencing template can be aided by 10–20 rounds of PCR using primers flanking the U-tag or tags. Conditions are adjusted to minimize any skewing of relative frequencies of individual tags. Once amplification has increased the probe amount to approximately $10^{15}$ copies, linear amplification can be accomplished with T7 DNA polymerase, primed by a T7 promoter included at the 3' end of one of the initial primers.

Figure 3:
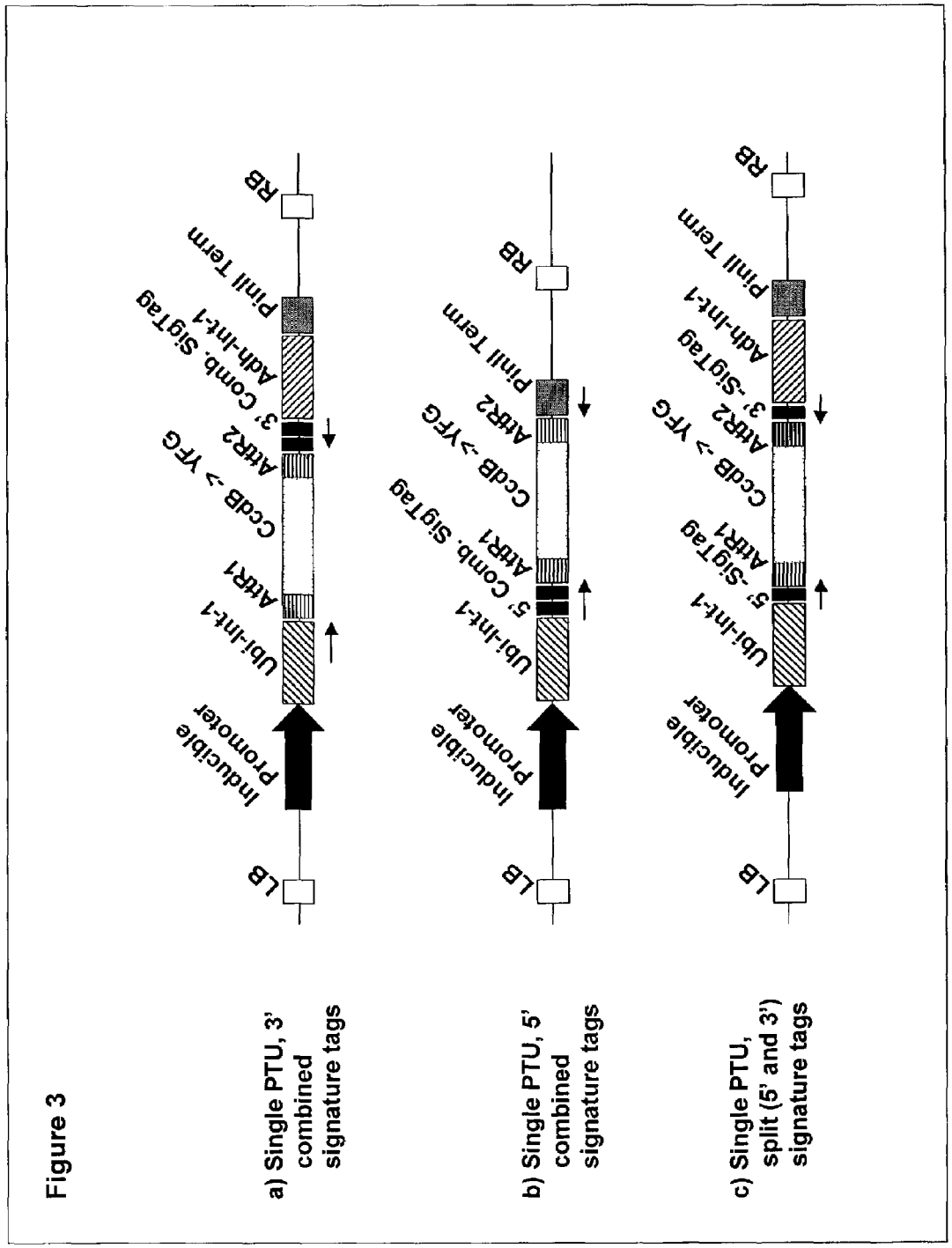
FIG. 3 depicts a construct design for a single PTU U-tag. These tags are shown located at several potential positions, including in the 3' UTR, the 5' UTR, or split locations with one tag in each of the 3' and 5' UTR. The small arrows in the figure represent possible gene rescue primer locations. The abbreviations LB and RB refer, respectively, to left and right T-DNA border.
Figure 4:
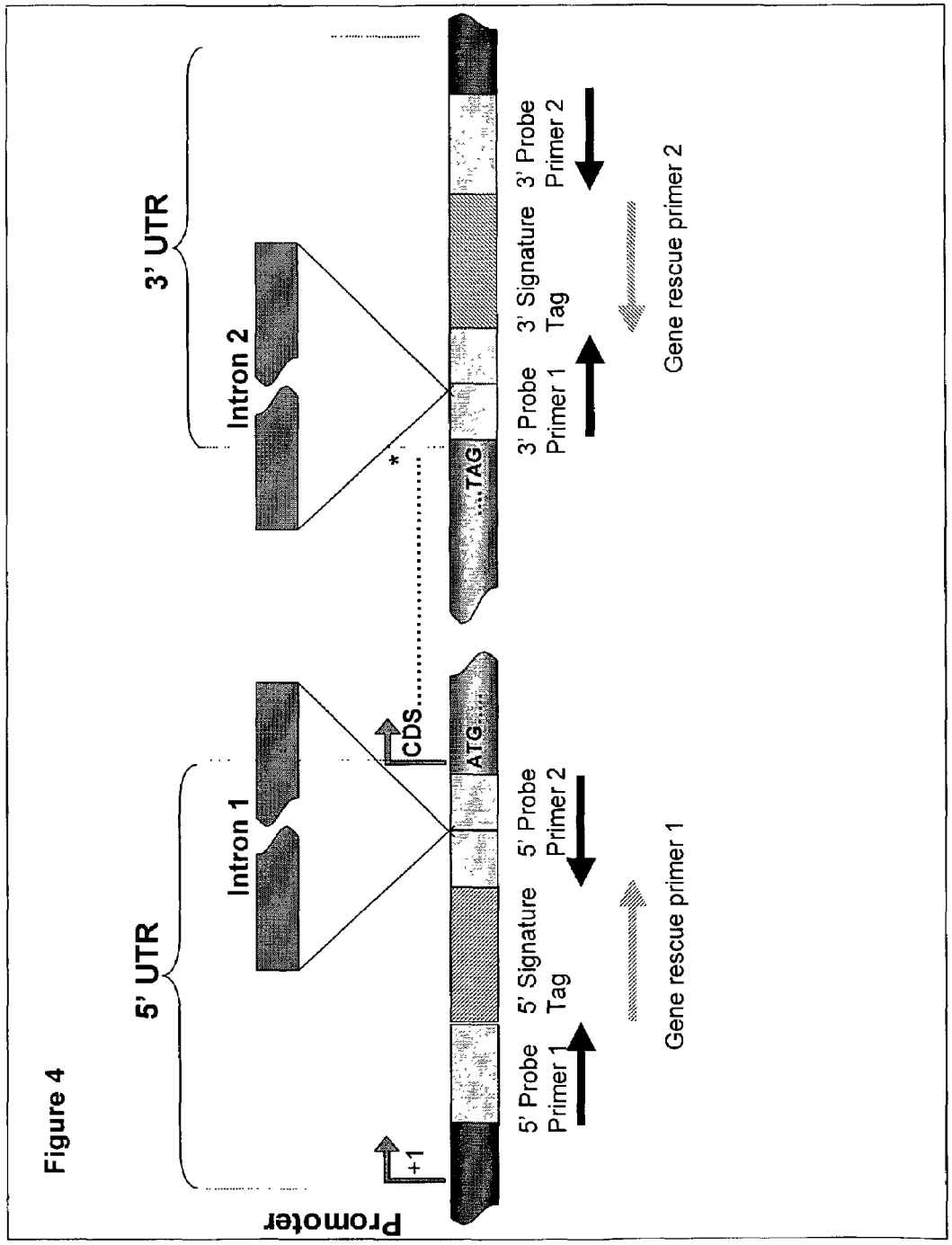
FIG. 4 depicts a split U-tag strategy, with one tag in the 5' UTR and the other in the 3' UTR of a coding sequence, flanked by PCR primers and driven by an inducible promoter. Introns interrupt one flanking primer in each pair to ensure that only cDNA, not genomic DNA, is amplified for probing. To rescue positives, PCR primers based on 5' and 3' tags are used to specifically amplify the coding region of a positive clone from cDNA or genomic DNA.

For sequence based detection methods, much larger U-tag populations can be used. One method of preparing U-tag templates for sequencing is shown in FIG. 3. The RT-PCR amplified U-tag domain contains flanking restriction enzyme sites that, when cleaved, result in self-ligatable ends to form a U-tag concatamer. Random juxtaposition of appropriate bases at low frequency at these fragment junctions results in reconstitution of a second, internal restriction site that allows cleavage of the concatamers into clonable fragment sizes each of which "reads out" 30 or more U-tag sequences.

After "hit" U-tags are identified, the candidate clone containing the "hit" U-tag or tags and a nucleotide sequence of interest must be identified and isolated. This can be done through several methods. In one method, the original pool of clones used for expression in the host cell can be arrayed to allow the U-tag containing a "hit" clone to be identified using the U-tag or tags as labeled probes. Another method to identify candidate clones is by long-range PCR followed by nested PCR. The U-tag plus a second primer flanking the candidate nucleotide sequence of interest is used to amplify a larger region containing the entire candidate nucleotide sequence of interest, and then nested primers directly flanking the nucleotide sequence of interest are used to amplify sequenceable DNA.

In methods of identifying and isolating "hit" U-tags that comprise hybridization techniques, all or part of a known nucleotide sequence is used as a probe that selectively hybridizes to other corresponding nucleotide sequences present in the library population. By "population" a group or collection is intended. The hybridization probes may be cDNA fragments, genomic DNA fragments, RNA fragments, or other oligonucleotides, and may be labeled with a detectable group such as $^{32}P$ or any other detectable marker.

Thus, for example, probes for hybridization can be made by labeling synthetic oligonucleotides based on the non-redundant U-tag sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

In methods that are comprised of a PCR approach, methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York) all of which are herein incorporated by reference. Known methods of PCR include, but are not limited to, methods using paired primers, nested primers, single specific primers, degenerate primers, gene-specific primers, vector-specific primers, partially-mismatched primers, and the like.

By "generating a library" the cloning of many plasmids containing one or more non-redundant U-tags in the first DNA construct and inserting operably linked nucleotide sequences of interest in the first or second DNA construct of the plasmid is intended. In one embodiment, the plasmids of the library will contain a first DNA construct. In another embodiment the plasmids of the library will contain a first DNA construct and a second DNA construct. By "operably linked" a functional linkage between sequences, wherein transcription may be initiated in one sequence and transcription continues throughout the operably linked sequences is intended. Generally, operably linked means that the nucleic acid sequences being linked are contiguous and, where necessary to join two protein coding regions, contiguous and in the same frame. A sequence operably linked to a multiple cloning site will allow transcription of a nucleotide sequence of interest inserted in the multiple cloning site. The library plasmids may additionally contain selectable marker genes.

In one embodiment, the first DNA construct includes a reporter sequence operably linked to one or more U-tags operably linked to an mRNA stabilizing sequence operably linked to a transcriptional regulatory region. This embodiment allows identification of a nucleotide sequence in the second DNA construct that modulates the activity of the transcriptional regulatory region of the first DNA construct. The first DNA construct may contain a transcriptional regulatory region known to function in a physiological pathway of interest. The nucleotide sequence in the second DNA construct may encode a peptide, polypeptide, protein, or RNA that modulates the activity of the transcriptional regulatory region of the first DNA construct directly or indirectly. A polypeptide encoded by the nucleotide sequence of the second DNA construct may directly bind the transcriptional regulatory region or may modulate a component of a physiological pathway to which the transcriptional regulatory region responds, thus indirectly modulating the activity of the transcriptional regulatory region. Alteration of the activity of the transcriptional regulatory region would cause an increase or decrease in the level of the reporter sequence operably linked to the U-tag or tags. Any transcriptional regulatory region that responded to a particular activator or treatment would result in modulation of U-tag signature levels. A modulation of the U-tag signature levels would indicate an involvement of the nucleotide sequence of interest from the second DNA construct with the physiological pathway of interest in which the transcriptional regulatory region is known to function.

An embodiment of the invention is the search for transcriptional regulatory regions that respond to a particular gene or treatment. In this embodiment, the first DNA construct includes a reporter sequence operably linked to one or more U-tags operably linked to an mRNA stabilizing sequence operably linked to a multiple cloning site. The multiple cloning site is provided with a plurality of restriction sites for insertion of a library of nucleotide sequences of interest. Inserts of nucleotide sequences of interest in the first DNA construct will be potential transcriptional regulatory regions of interest. The nucleotide sequence of interest may be known transcriptional regulatory regions or nucleotide sequences that have been mutagenized randomly or in a site-specific manner, promoter fusions, and transcriptional regulatory regions altered by insertion or deletion of enhancer elements or transcription factor binding sites. The transcriptional regulatory regions may respond to a particular gene or treatment by increasing or decreasing the level of transcription of the reporter sequence operably linked to the U-tag or tags. Any transcriptional regulatory region that responded to a particular activator or treatment would result in modulation of U-tag signature levels. The embodiment allows identification of transcriptional regulatory regions that respond to treatment by an agent, for example, a safener, a pharmaceutically active compound, small molecule, peptide, or protein.

By "reporter sequence" an open reading frame that gives rise to a reasonably stable mRNA without regard to the polypeptide produced, including but not limited to, green fluorescent protein (GFP), blue fluorescent protein (BFP), beta-glucuronidase (GUS), or luciferase is intended. Methods for detection and quantification of GFP, BFP, Gus, and luciferase are well known in the art. A fusion of the maize transcription factors C and R has also been used as an in vivo color marker for gene expression in maize. Some candidate nucleotide sequences will be quite rare in a library population, on the order of one in a million or less. Another way of increasing the throughput of a U-tag screen is to use visual identification of "hit-containing" sample pools which are then the focus of RNA extraction and U-tag readout experiments. Use of visually detectable U-tagged reporters such as GFP allows an increase in the assay throughput. For visualization in vivo, a GFP with a nuclear localization signal may provide the best marker for distinguishing single cells. The above list of reporter sequences is not meant to be limiting. Any reporter gene or sequence may be used in the present invention.

The choice of placement of one or two U-tags in the 3' or 5' UTR of the reporter sequence in the first DNA construct is dictated by convenience and experimentation to determine which location gives the most consistent tag signal during transient expression. Both 3' and 5' UTRs contribute to message stability and other factors may influence the ultimate levels of mRNA produced. If appropriately designed, the tag or tags could even be included in the coding region of the transcript, giving rise to a protein fusion at the amino- or carboxy-terminus of the reporter gene. Such a tag could be designed to minimize stop codons or other features that might interfere with reporter function.

By "mRNA stabilizing sequence" sequences, such as polyadenylation signals, that increase the half-life of mRNA molecules in the cell are intended. In the methods of the present invention, the DNA encoding such mRNA stabilizing sequences is operably linked to the reporter construct or a U-tag. For a 3'-UTR tag, suitable polyadenylation signals are those polyadenylation signals that can be modified without loss of transcript processing or stability, such as a 315 nucleotide fragment of the potato proteinase inhibitor II terminator region (GenBank Accession Number X04118) or the 315 nucleotide PinII terminator. One of skill in the art will recognize other stabilizing sequences that can be used in the methods of the invention.

The second DNA construct will include 5' and 3' regulatory sequences operably linked to a nucleotide sequence of interest or a multiple cloning site. The multiple cloning site provides a plurality of restriction sites for insertion of nucleotide sequences of interest or a library of nucleotide sequences of interest to be under the transcriptional regulation of the regulatory regions. The second DNA construct will include, in the 5' to 3' direction of transcription, a transcriptional and translational initiation region, a nucleotide sequence of interest, and a transcriptional and translational termination region functional in the host cell into which it is introduced. The transcriptional regulatory region may be native, or analogous or foreign or heterologous to the host cell or to the nucleotide sequence of interest. The promoter may be a natural sequence or alternatively a synthetic sequence. By "foreign" it is intended that the transcriptional initiation region is not found in the host cell into which the plasmid is introduced. By "heterologous" it is intended that the transcriptional initiation region is operably linked to a nucleotide sequence of interest that is not native to the transcriptional initiation region.

The second DNA construct may additionally contain 5' leader sequences in the second DNA construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126–6130); potyvirus leaders, for example, TEV leader (Tobacco Etch Virus) (Gallie et al. (1995) *Gene* 165(2):233–238), MDMV leader (Maize Dwarf Mosaic Virus) (*Virology* 154:9–20), and human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, N.Y.), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In both the first and second DNA constructs, the termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991)*Mol. Gen. Genet.* 262:141–144; Proudfoot (1991) *Cell* 64:671–674; Sanfacon et al. (1991) *Genes Dev.* 5:141–149; Mogen et al (1990) *Plant Cell* 2:1261–1272; Munroe et al (1990) *Gene* 91:151–158; Ballas et al (1989) *Nucleic Acids Res.* 17:7891–7903; and Joshi et al (1987) *Nucleic Acid Res.* 15:9627–9639.

Additional sequence modifications are known to enhance gene expression in a cellular host. These modifications may be useful for the reporter sequence of the first DNA construct or for the nucleotide sequence of interest in the second DNA construct. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the first and second DNA constructs, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

By the "nucleotide sequence of interest" nucleotide sequences obtained from cDNA, genomic DNA, in vitro mutagenized or recombined DNA or any complex population of molecules is intended. The nucleotide sequences of the invention are open reading frames or fragments of open reading frames that encode polypeptides or polypeptide fragments. In another embodiment the nucleotide sequences of the invention are transcribed into a population of antisense or hairpin sequences. The candidate library of nucleotide sequences of interest is generated by methods particular to the library type (cDNA, genomic DNA, or in vitro mutagenized molecules) and the source (plant, mammalian, animal, fungal, or bacterial cells, or in vitro reaction). Mutagenized nucleic acid sequences may be obtained by any method known to one of skill in the art, including but not limited to, site directed mutagenesis, UV irradiation, chemical treatment, passage through mutagenic strains, and exposure to modifying agents. The nucleotide sequences of interest must have clonable ends that allow high efficiency ligation into the multiple cloning site of the first or second DNA construct. Start and/or stop codons can be provided in the second DNA construct, or the nucleotide sequences of interest may include start and stop codons. Methods of library construction are well known to one of skill in the art (Ausubel, et al (1995) *Current Protocols in Molecular Biology*, Greene Publishing and Wiley-Interscience, New York; Sambrook et al. (1989) *Molecular Cloning: A Laboratory Manual* (2d ed., Cold Spring Harbor Laboratory Press, Plainview, N.Y.).

By "transcriptional regulatory region" a nucleotide sequence comprising promoters or enhancer regions is intended. Enhancer regions must be operably linked to a promoter region capable of driving expression in the host cell of interest. A number of promoters can be used in the practice of the invention. The promoters can be selected based on the desired outcome. Generally, constitutive promoters should be used in the second DNA construct while inducible or tissue-preferred promoters or promoters known to be involved with a desired physiological pathway should be used in the first DNA construct.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992)

*Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142.

Pathogen-inducible promoters would be beneficial for study of the pathogen response pathway in plants. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116. See also WO 99/43819, herein incorporated by reference.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Mol. Gen. Genet.* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189–200). In an embodiment of the invention, a defense inducible promoter operably linked to one or more U-tags in the first DNA construct is used for high through put analysis of expression of candidate R genes.

Wound-inducible promoters would be beneficial for the study of the plant response to physical damage or wounds. Such wound-inducible promoters include potato proteinase inhibitor (pin II) gene (Ryan (1990) *Ann. Rev. Phytopath.* 28:425–449; Duan et al. (1996) *Nature Biotechnology* 14:494–498); wun1 and wun2, U.S. Pat. No. 5,428,148; win1 and win2 (Stanford et al. (1989) *Mol. Gen. Genet.* 215:200–208); systemin (McGurl et al. (1992) *Science* 225: 1570–1573); WIP1 (Rohmeier et al. (1993) *Plant Mol. Biol.* 22:783–792; Eckelkamp et al. (1993) *FEBS Letters* 323: 73–76); MPI gene (Corderok et al. (1994) *Plant J.* 6(2): 141–150); and the like, herein incorporated by reference.

Chemically regulated promoters would be beneficial for the study of the responses to elicitor compounds. Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

Other inducible promoters of interest include the E-selectin promoter, the migA promoter (Yang et al. (2000) *Microbiology* 146:2509–2519), IpcI, NF-KB, heavy metal-inducible human metallothionein IIA promoter, P1 and P3 of *Pseudomonas aeruginosa* (Schurr, et al (1995) *J. Bacteriol* 177:5670–5679). Commonly used promoters for expression in mammalian cells are derived from polyoma, Adenovirus 2, cytomegalovirus, and Simian Virus 40. For other suitable expression systems for both prokaryotic and eukaryotic cells, see chapters 16 and 17 of Sambrook et al. (1989) *Molecular cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.).

Tissue-preferred promoters would be beneficial for the study of differentiation or development. Tissue-preferred promoters include those disclosed in Yamamoto et al. (1997) *Plant J.* 12(2):255–265; Kawamata et al. (1997) *Plant Cell Physiol* 38(7):792–803; Hansen et al. (1997) *Mol. Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol. Biol.* 23(6): 1129–1138; Matsuoka et al. (1993) *Proc Natl. Acad. Sci. USA* 90(20):9586–9590; and Guevara-Garcia et al. (1993) *Plant J.* 4(3):495–505.

Suitable tissue-specific promoters include the albumin promoter (e.g., liver-specific promoter; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; see, U.S. Pat. No. 4,873,316 and EP 264,166). Developmentally-regulated promoters are also encompassed, for example the murine hox homeobox promoters (Kessel and Gruss (1990) *Science* 249:374–379), the α-fetoprotein promoter (Campes and Tilghman (1989) *Genes Dev.* 3:537–546), and the like. Such promoters can be modified, if necessary, for weak expression.

Depending on the desired results, weak promoters may be beneficial. Where low level expression is desired, weak promoters will be used. Generally, by "weak promoter" a promoter that drives expression of a coding sequence at a low level is intended. By "low level" levels of about 1/1000 transcripts to about 1/100,000 transcripts to about 1/500,000 transcripts are intended. Alternatively, it is recognized that weak promoters also encompass promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example, the core promoter of the Rsyn7 promoter (WO 99/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

Generally, the plasmids of the library will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), G418, hygromycin, and methotrexate, as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.* 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Sci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334:721–724. Such disclosures are herein incorporated by reference.

The above list of selectable marker genes is not meant to be limiting. Any selectable marker gene can be used in the present invention.

The method of transformation employed will depend on the tissue type, volume of tissue, and whether or not stable or transient transformation is desired. Once the appropriate inoculation concentration and library pool size is determined, an appropriate amount of tissue is chosen to allow for multiple copies of each library member to be delivered to a cell. Ideally, the number of independent cells receiving each candidate gene should be at least in the hundreds.

The plasmids of the invention can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboratory Manual* (2d ed., Cold Spring Harbor Laboratory Press, Plainview, N.Y.) and other laboratory manuals.

Transformation protocols, as well as, protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, *Agrobacterium*-mediated transformation (U.S. Pat. No. 5,563,055; U.S. Pat. No. 5,981,840), direct gene transfer (Paszkowski et al. (1984) *EMBO J.* 3:2717–2722), and ballistic particle acceleration (see, for example, U.S. Pat. No. 4,945,050; U.S. Pat. No. 5,879,918; U.S. Pat. No. 5,886,244; U.S. Pat. No. 5,932,782; McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P: 175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); U.S. Pat. No. 5,240,855; U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

After incorporating the library of plasmids into host cells, the host cells must be cultured for a sufficient duration to allow expression from the second DNA construct and transcription from the transcriptional regulatory region. Incorporating the library into host cells may be accomplished by any means known to one of skill in the art, including but not limited to, transforming or transfecting host cells. The kinetics of the promoter (or cell death process) being used to control the time of harvest for optimal detection of differential U-tag expression. This can be determined by using quantitative PCR to track mRNA levels after delivery of a known positive control gene.

As noted, the compositions and methods of the invention can be used to identify nucleotide sequences that modulate regulatory regions of a physiological pathway of interest. By "physiological pathway of interest" any biological process that has a genetic component including, but not limited to, increased expression of a polypeptide, decreased expression of a polypeptide, increased transcription of a nucleotide sequence, decreased transcription of a nucleotide sequence, increased replication of a nucleotide sequence, and decreased replication of a nucleotide sequence is intended.

The physiological pathways of interest include but are not limited to, signal transduction; housekeeping; insect resistance; pathogen resistance; herbicide resistance; reproduction; sterility; carbohydrate, polypeptide, nutrient, oil, and starch metabolism; carbohydrate modifications; growth; detoxification; male or female gametophytic development; disease progression, cancer development, tissue and organ differentiation; tissue, organ, and organism development; apoptosis; toxicity; cell senescence; recombination; mutagenesis; DNA repair; stress response; heat shock response; osmotic response; angiogenesis; congenital disorders; replication; transcription; translation; R-gene mediated response; and pathogen response.

The method can be used to investigate physiological pathways of interest in numerous cell types, including but not limited to plant, animal, mammalian, fungal, and bacterial cells. Suitable mammalian cells include, but are not limited to, Chinese hamster ovary cells (CHO) or COS cells. Suitable tissue types include, but are not limited to, healthy and diseased lung, spleen, brain, colon, liver, skin, thyroid, uterus, endometrium, ovary, prostate, breast, immune cells, bone marrow, heart, nerve, blood vessel, thymus, kidney, testis, muscle, pancreas, and small intestine.

A preferred tissue for high throughput assays in maize is Black Mexican Sweet (BMS) tissue cultures. However, maize tissues from other sources can be used. A number of plant tissues can be used, including but not limited to, immature embryos, infiltrated leaves, hypocotyls, or root tissues.

The present invention may be used to investigate physiological pathways of interest of any plant species, including, but not limited to, monocots and dicots. Examples of plant species of interest include, but are not limited to, corn (*Zea mays*), *Brassica* sp. (e.g., *B. napus*, *B. rapa*, *B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, *Brassica*, soybean, cotton, safflower, peanut, sorghum, wheat, millet, tobacco, etc.), more preferably corn and soybean plants, yet more preferably corn plants.

An embodiment of the invention is a high throughput assay for the screening of libraries in *Agrobacterium*, described elsewhere herein. The high throughput assay is performed in BMS cells, or any cell line suitable for mass quantity production. The high throughput assay is not reliant upon the U-tag compositions or methods, as identification of positive clones occurs through the use of identified wells in tissue culture plates. The tissue culture plates used in the methods of the invention are typically 96 well plates; however, other multi-well plates, such as 386 well plates or 1536 well plates may be used in the embodiment. All liquid handling and transfers between plates is performed using a multi-channel pipettor or an automation machine such as, but not limited to, SciClone, Hamilton MPH96, Titertek, Matrix, or Q-Bot. A library of plasmids containing nucleotide sequences of interest operably linked to a promoter capable of initiating transformation in plant cells is transformed into *Agrobacterium*. The *Agrobacterium* cells are used to inoculate BMS cells containing a promoter operably linked to a reporter gene, such as GUS, GFP, or luciferase. After co-cultivation of the *Agrobacterium*-BMS cells for one or two days, the cells are assayed for a gain or loss of function of the gene of interest or an alteration in expression level of a reporter gene.

As indicated, the compositions and methods of the invention can be used to identify transcriptional regulatory regions that are modulated by an agent of interest.

EXAMPLES

This invention can be better understood by reference to the following non-limiting examples. It will be appreciated by those skilled in the art that other embodiments of the invention may be practiced without departing from the spirit and the scope of the invention as herein disclosed.

Example 1

Construction of the 3' UTR Signature Tag Recipient JT Parent Vector (Mod1)

This example describes a multi-step cloning process which was used to generate a dual plant transcription unit (PTU) 3' UTR combined signature tagged library. FIG. 1*a*) and 2 provide conceptual diagrams of the dual PTU, 3' UTR signature design. FIG. 1*b*) provides a conceptual diagram of a similar construct design, however, the signature tags are located in the 5' UTR.

The starting point for construction of the Mod1 vector was PHP8723 (11836 nt), a binary T-DNA parent construct (obtained from Japan Tobacco) containing a right T-DNA border (bp 11658–11682) followed by a plant transcription unit (PTU) as follows: a maize ubiquitin (Ubi) promoter region (bp 13–913), Ubi 5' untranslated region (bp 916–998), and Ubi-first intron (bp 999–2008) with a small portion of pUC18 multicloning site ending in NcoI (bp 2009 to 2029). This is followed by the *E coli* B-glucuronidase (GUS) open reading frame using the ATG of NcoI as a start codon (bp 2030 to 3838), followed by 56 bp of GUS 3' untranslated DNA (bp 3840 to 3894) followed by the Potato proteinase inhibitor II (PinII) terminator (bp 3895–4201). Downstream of this PTU (bp 4230–5543) is a PTU encoding phosphinothricin resistance (PAT) consisting of the CaMV 35S promoter linked to *Streptomyces* PAT followed by the CaMV 35S terminator. The T-DNA left border is at bp 5611–5643. The PHP8723 plasmid also contains Spectinomycin resistance (bp 6811–7599), a ColE1 origin of replication for high copy number in *E coli*. (8874–9143) and a bacteriophage lambda Cos site (bp 10157–10257) to facilitate recombination with the virulence plasmid PHP10523 in *Agrobacterium*.

To introduce 4 novel restriction sites in the 3' UTR region of PinII, which allows for cloning in the AdhI intron and also a 3' UTR signature tag set, 109 nucleotides of the 5' portion of PinII from 3839 to 3948 were replaced with a 53 nt multicloning sequence containing Bsu36I (C^CTAAG), AgeI (A^CCGGT), AscI GG^CGCGCC), and SgrAI (CA^CCGGCG) restriction sites. This replacement was accomplished by SOE cloning (Horton et al. (1993) Methods in Enzymol 217: 270–279).

To perform the SOE cloning, two rounds of PCR were used to first amplify two overlapping PCR fragments using PHP8723 as a template. The overlap region of the two PCR fragments contained the desired modifications designed via synthetic oligonucleotide primers, and incorporated sufficient template-homologous DNA to allow for base pairing under PCR conditions. The outermost PCR primer for each overlapping fragment was designed to flank a unique restriction site in the template that was subsequently preserved within the PCR product. A second round of PCR with the two overlapping fragments as self-templates (with the addition of sense and antisense primers that anneal to the 5' and 3' termini of these fragments) resulted in a combined fragment with desired base changes that, following digestion to generate sticky ends, was cloned back into these same restriction sites in template. In the case of PHP8723, an upstream BstBI (T^TCGAA) site in GUS (bp 3124) and a downstream NotI (GC^GGCCGC) site at the end of PinII (bp 4213) were used as cloning termini. The result of two rounds of SOE, gel purification, and enzyme digestion was a 1032 bp insert containing BstBI-NotI sticky ends and PinII modifications as desired.

PHP 8723 was doubly digested with BstBI and NcoI, phosphatased with alkaline phosphatase, and the 10747-pb BstBI-NotI backbone was gel-purified for subsequent ligation.

The 1032 bp BstBI-NotI SOE PCR product was ligated with the 10747 bp backbone of PHP8723 resulting in a 11779 bp construct with a truncated PinII terminator and 4 additional restriction sites just downstream of GUS. This construct was named Mod1 and the features are as follows: Ubi-ZMPro-Ubi-ZMIntron1-GUS-TrPinII JT Parent.

Addition of a 3' Intron to the 3' UTR Signature Tag Recipient JT Parent Vector (Mod2)

The above construct (Mod1) was digested with Bsu36I and AgeI, phosphatased, and gel-purified for subsequent ligation.

The AdhI intron was PCR-amplified from PHP8773, which contains the 538 bp AdhI intron as part of a different PTU. PCR was accomplished using the following oligos designed to amplify a fragment that, following digestion with Bsi36I and AgeI, resulted in a 544 bp fragment which was ligated with the Bsu36I-AgeI-digested Mod1 backbone. The design of oligos for use in PCR is well known to those skilled in the art. The required oligo design is dependent upon the intron being added and the parent vector being used.

The resulting construct was Mod2, having the following features: Ubi-ZMPro-Ubi-ZMIntron1-GUS-AdhIntron-TrPinII JT Parent and a length of 12313 bp.

Efficiency of the Mod2 construct was compared to those of the PHP8723 (original, or control) and the Mod1 constructs. Each construct was independently electroporated into competent LBA4404 Agrobaterium cells already harboring a plasmid, PHP10523 containig Vir genes for T-DNA transfer, an *Agrobacterium* low copy number plasmid origin of replication, a tetracycline resistance gene, and a Cos site for in vivo DNA bimolecular recombination. Transformants were selected on LB agar+Spectinomycin. Transformants contain a cointegrate plasmid (designated JT Agro) resulting from recombination of the introduced plasmid with the resident PHP10523 plasmid. The cointegrate plasmid is maintained due to the *Agrobacterium* origin of replication from 10523 together with Spectinomycin selection from the introduced plasmid. *Agrobacterium* cells harboring cointegrate (JT Agro) forms of PHP8723, Mod1, or Mod2 were co-cultivated with maize Black Mexican Sweet (BMS) cell cultures using protocols outlined elsewhere in this application. Transient expression of the GUS gene, induced after co-cultivation, was visualized by X-Gluc staining and compared. Though intensity of GUS staining for Mod2 was slightly decreased as compared to GUS staining for PHP8723 and Mod1, it is still sufficient to be used in high-throughput experiments. These results indicate that the insertion of an intron in the a plant 3' UTR has no significant detriment to gene expression, and provides a basis for RNA-specific signature tag amplification and detection.

Removal of PAT Open Reading Frame and Insertion of AttR1-ccdA-ccdB-AttR2 (Mod3)

Partial digestion of the Mod2 plasmid (12313 bp) is carried out using BgIII (A^GATCT) and Acc65I (G^GTACC). The resulting 11751 bp fragment representing BgIII at 5801 to Acc65I at 5239 bp is gel purified using 0.75% agarose. The two 5' overhangs are filled in using dNTP's in the presence of Klenow fragment (Maniatis).

A blunt ended fragment is prepared consisting of Invitrogen's Gateway AttR1 and AttR2 recombination sites flanking the *E coli* ccdA-ccdB genes and promoter (Hartley et al., 2000, Genome Research 10:1788–1795). This fragment is 1002 bp and lacks the chloramphenicol resistance gene found in the usual Gateway destination vector (this is removed as a BamHI fragment of 703 bp).

The blunt-ended insert is ligated together with Klenow'ed Mod2 backbone from above using T4 ligase (Roche) and used to transform *E coli* DH5 alpha. This results in loss of one of 2 BgIII sites found in the parent Mod2.

The resulting 12757 bp plasmid results in the construct named Mod3 which has the following features: Ubi-ZMPro-Ubi-ZMIntron1-AttR1-ccdB-AttR2-AdhIntron-TrPinII JT Parent.

Removal of the Ubi Promoter and Insertion of an Inducible Promoter (e.g. Pr1-81) (Mod4)

The Mod3 plasmid is subjected to partial digestion by HindIII, followed by BglII digestion. The 11800 bp partial digestion fragment defined by BglII (959) to HindIII (2) is phosphatased and gel-purified. PHP17398 (5582 bp) containing the PR1-81 promoter from maize is digested with HindIII and BamHI, and a 1012 bp Hind-Bam fragment containing the PR1-81 promoter is gel-purified.

The PR1-81 fragment is ligated with the Mod3 partial digest and transformed into *E coli* DH5 alpha. The resulting 12812 bp plasmid is Mod4, with features as follows: PR1-81-Ubi-ZMIntron1-AttR1-ccdB-AttR2-AdhIntron-PinII JT Parent.

Creation of the 3' Signature Tagged JT Parent Library (Mod4ST-Dest-lib)

Preparation of the U-Tags by Oligonucleotide Synthesis

The U-tags may be created in a variety of ways, such as by oligonucleotide synthesis as described herein. Oligonucleotide synthesis is carried out in such a way as to create redundancy in sequence over sufficient nucleotides to give the desired signature population size. This example describes the preparation of 28-mer and 56-mer tags, however, 24-mer and 48-mer tags can also be used.

A series of sense and complementary antisense 5' phosphorylated oligonucleotides are synthesized that, when annealed together, create SgrAI-AflII restriction sites flanking a 56-nucleotide signature domain, according to the design indicated in Table 1, resulting in a 1024-fold diverse tag population. Table 2 represents an alternative design in which two separate 28-bp signature tags are used. Every oligo in the set differs from every other oligo by at least one or more base pairs (preferably 16 or more) in the 56-bp signature domain. This is termed a combined signature tag set.

TABLE 1

Combined signature tag oligo design using G + C + A + T-matched blocks of 4 or 8

Combined signature tag (concatenation of two, 28-mer half-tags = 56 bp total)
Minimum mismatch among half-tags = 8 bp out of 28
Minimum mismatch among full length-tags = 16 bp out of 56

| BLOCK 1 | BLOCK 2 | BLOCK 3 | BLOCK 4 | BLOCK 5 | BLOCK 6 |
|---|---|---|---|---|---|
| GTCA | GATC | TGAC | CGTA | CTAG | CATG GTCA |
| ACGT | ATCG | ACTG | ACGT | AGTC | GTAC CAGT |
| CATG | TCGA |  | TACG |  | ACGT AGTC |
| TGAC | CGAT |  | GTAC |  | TGCA TCAG |
| 4 | x 4 | x 2 | x 4 | x 2 | x 4 |

Half-tag Fold Diversity: 4 × 4 × 2 × 4 × 2 × 4 = 1024

| BLOCK 7 | BLOCK 8 | BLOCK 9 | BLOCK 10 | BLOCK 11 | BLOCK 12 |
|---|---|---|---|---|---|
| GTCA GATC |  | CGTA |  | CATG | GTCA |
| ACGT ATCG |  | ACGT |  | GTAC | CAGT |
| CATG TCGA | GACT | TACG | GACT | ACGT | AGTC |
| TGAC CGAT | CTGA | GTAC | TCGA | TGCA | TCAG |
| 4 | x 2 | x 4 | x 2 | x 4 | x 4 |

Half-tag Fold Diversity: 4 × 2 × 4 × 2 × 4 × 4 = 1024
Combinatory Diversity (full-length tags) = $(1024)^2$ = 1.048 × $10^6$

TABLE 2

A split signature tag design using G + C + A + T-matched blocks of 4 or 8

5' signature tag (28-mers).
Minimum mismatch among tags = 8 bp out of 28

| BLOCK 1 | BLOCK 2 | BLOCK 3 | BLOCK 4 | BLOCK 5 | BLOCK 6 |
|---|---|---|---|---|---|
| GTCA | GATC | TGAC | CGTA | CTAG | CATG GTCA |
| ACGT | ATCG | ACTG | ACGT | AGTC | GTAC CAGT |
| CATG | TCGA |  | TACG |  | ACGT AGTC |
| TGAC | CGAT |  | GTAC |  | TGCA TCAG |
| 4 | x 4 | x 2 | x 4 | x 2 | x 4 |

Fold Diversity: 4 × 4 × 2 × 4 × 2 × 4 = 1024
3' Signature tag (28-mers). Minimum mismatch among tags = 8 bp TABLE 2-continued A split signature tag design using G + C + A + T-matched blocks of 4 or 8

Minimum mismatch with 5' signature tags = 8 bp

| BLOCK 1 | BLOCK 2 | BLOCK 3 | BLOCK 4 | BLOCK 5 | BLOCK 6 |
|---------|---------|---------|---------|---------|---------|
| GTCA GATC |  | CGTA |  | CATG | GTCA |
| ACGT ATCG |  | ACGT |  | GTAC | CAGT |
| CATG TCGA | GACT | TACG | GACT | ACGT | AGTC |
| TGAC CGAT | CTGA | GTAC | TCGA | TGCA | TCAG |
| 4 | 2 | 4 | 2 | 4 | 4 |

Fold Diversity: $4 \times 2 \times 4 \times 2 \times 4 \times 4 = 1024$
Combinatory Diversity (5' + 3' tags) = $(1024)^2 = 1.048 \times 10^6$ The two half-signature tags (left and right 28-bp halves of the 56-mer tag, respectively, in the example given) differ among themselves (and from every member of the other half-tag population) by at least one bp (preferably 8 bp or more). The two half-tag domains may be separated by a series of non-GATC balanced deoxynucleotides such as AAAA or TTTT to minimize any significant hybridization across tags.

The base immediately 5' of the SgrAI-compatible overhang is mutated from A to C to destroy the SgrAI site on ligation. One strand of the oligo can be designed without a 5' phosphate group, to prevent concatenation. In this case, the vector is not dephosphorylated.

After synthesis and purification, oligos are mixed in equimolar amounts, heated to 95° C. and allowed to anneal under conditions that allow every oligo to find its complement. The result is a population of oligo duplexes with sticky ends, ready for ligation into Mod4. Since every member differs from every other member by at least 8 bp, only exact complements should anneal.

At least 10 micrograms of Mod4 DNA are digested with AscI (Roche) and SgrAI (NEB). Following digestion, the DNA is dephosphorylated with alkaline phosphatase, and then the phosphatase enzyme is heat-inactivated. The resulting 12801 bp fragment is gel purified.

The signature tag oligo set is ligated at a 10:1 molar ratio using T4 DNA ligase. A control ligation in which no oligos are present is included. The ligase is heat-inactivated. To eliminate singly-cut and relegated molecules, both ligation mixtures are digested with SgrAI. Any resulting linearized molecules should not significantly contribute to the transformation pool.

The ligated, digested DNA is purified by agarose gel or other suitable method. Using the purified ligated DNA, sufficient electrocompetent DH5 alpha *E coli* cells to recover a minimum of 5×10⁶ independent colonies (ligation efficiency is determined in preliminary experiment) are transformed. This may require repeated independent ligation/transformations. The library is amplified in suitable broth or other media containing Spectinomycin. The amplified library is stored at –80° C. in glycerol. This construct is now referred to as Mod4 signature tagged destination JT Parent library, or Mod4ST-Dest-Lib.

Example 2

*Agrobacterium*-Mediated Transient or Stable Transformation of Maize Cells

For *Agrobacterium*-mediated transformation of maize cells with a plasmid library of the invention, preferably the following method is used. Media recipes follow. *Agrobacterium tumefaciens* cells are cultured on solid 800 medium and incubated at 27° C. in the dark for one day. A single colony is transferred to solid 810 medium and incubated at 27° C. in the dark for two days. *Agrobacterium* from the 810 plate is suspended in #561Q liquid medium containing 0.1 mM Acetosyringone to a density at O.D550 nm=0.25. It is ready for co-cultivation with BMS cells.

Black Mexican Sweet (BMS) cells are maintained in #237 medium. The cells are collected by gravity. Under a tissue culture hood, the supernatant is removed and the BMS cell pellet is washed three times with #561Q+0.1 mM Acetosyringone. The pellet from the last wash is diluted at a ratio of 1:3 (v/v) with #561 Q+0.1 mM Acetosyringone and is ready for co-cultivation with *Agrobacterium*.

Media Recipes 561Q comprises 4 g/l CHU(N6) Basal Salts (Sigma C-1416), 1 ml/l Eriksson's Vitamin Mix (1000× Sigma-1511), 0.5 mg/l Thiamine HCl, 1.5 mg/l 2,4-dichlorophenoxyacetic acid, 0.69 g/l L-Proline, 68.5 g/l sucrose, and 36 g/l glucose at pH 5.3.

237 comprises 4.3 g/l MS Salts (Gibco 11117), 0.1 g/l myo-inositol, 5 ml/l MS Vitamin Stock Solution, 2 mg/l 2,4-dichlorophenoxyacetic acid, and 30 g/l sucrose at pH 5.6.

MS Vitamin Stock Solution (36J) comprises 0.1 g/l nicotinic acid, 0.02 g/l thiamin-HCl, 0.1 g/l pyridoxine-HCl, and 0.4 g/l glycine brought to volume with polished D-I H₂O.

Example 3

Mobilization of Test Library into Signature-Tagged Destination Library and Insertion into *Agrobacterium* T-DNA Using the Gateway Recombination Cloning Method (Mod4ST-Expr-JT Agro)

Any collection of one or more open reading frames (ORF's) can be introduced into the second promoter-terminator cassette of the Mod4ST-Dest-Lib, driven by a second, constitutive promoter (CaMV 35-S). In some cases an ATG start codon is required upstream of the inserted DNA; in other cases the ORF's will include a start codon. Also, a stop codon may or may not be required downstream. Examples of suitable ORF's include a collection of cDNA's from a tissue of interest, a collection of related genes that has been subjected to recombination in vitro or in vivo by one or more techniques (see, U.S. 2002/0102734 A1; and U.S. Pat. No. 6,420,175); a collection of EST clones of interest, or PCR derivatives from these sources.

The collection of one or more ORF's as described above is prepared in an Invitrogen Gateway entry vector with flanking AttL1/AttL2 sites. See Invitrogen's Gateway literature at www.invitrogen.com for detailed methods and options for doing this. The library DNA is prepped according to Invitrogen's published methodology for gateway cloning.

An aliquot of the amplified, Mod4ST-Dest-Lib is lysed and extracted to obtain plasmid DNA which is adjusted to an appropriate concentration according to Invitrogen's Gateway protocols for L/R cloning. *Agrobacterium* strain LBA4404 or equivalent, containing the plasmid PHP10523 (containing VIR genes, a T-DNA Origin of replication, and Tetracyline resistance), is made competent for transformation by electroporation.

The entry and destination clones are mixed and incubated with appropriate reagents (including LR Clonase) from Invitrogen, and the entire reaction mixture is introduced into *Agrobacterium* LBA4404 competent cells via electroporation, at a scale sufficient to generate a number of viable transformants greater than or equal to the desired sample size for high-through-put (HTP) assay. This could be up to $10^5$ transformants or even more. Repeated transformations and/or ligations may be required to accomplish this, depending on the transformation efficiency of the competent cells.

The transformation mixture is allowed to recover in SOC medium for 3 hrs, (SOC=Bacto-tryptone 20 g; Yeast extract 5 g; NaCl 0.584 g; KCl 0.186 g; Mix components and adjust pH to 7.0 with NaOH and autoclave; Add 1 ml of 2 M Mg++stock to 99 ml medium). The library may be amplified overnight by growing cells in liquid broth medium including Spectinomycin. The resulting library is the Mod4 signature-tagged expression JT Agro library in LBA4404 or equivalent *Agrobacterium* cells (Mod4ST-Expr-JT Agro).

Co-Cultivation of BMS Cells

The transformed Agro cells containing Mod4ST-Expr-JTA are grown to mid-log phase in suitable liquid broth medium containing spectinomycin and acetylsyringone (which is used to induce Vir functions in the T-DNA to allow T-DNA transfer). Equal aliquots of Agro cells are added to two or more suspension cultures of Black Mexican Sweet (BMS) corn in liquid medium, according to the optimized protocol for BMS transient assays known in the art. The cultures are harvested at two or more time points previously determined to be optimal for detection of promoter activation, and immediately frozen for RNA extraction A duplicate aliquot of the Agro cells is used to extract plasmid DNA for later clone rescue.

The frozen BMS cultures are extracted for total RNA using standard procedures. Total RNA is used as a template for $1^{st}$ strand cDNA synthesis with Superscript II (Invitrogen), using an antisense primer containing a T7 promoter to make signature tag-specific $1^{st}$ strand cDNAs, using instructions provided by the manufacturer. Incubation is stopped by incubating at 65° C. at alkaline pH in the presence of EDTA.

Second strand synthesis is obtained using DNA Polymerase 1 in the presence of RNAse H at DNA ligase (Invitrogen). RT-PCR oligonucleotide primers are designed as appropriate for amplifying a hybridization probe. The design of RT-PCR oligonucleotide primers is well known by those skilled in the art.

In this particular example, the antisense primer as discussed above must be paired with a second primer flanking the Adh intron/exon junction. These primers bind to cDNA from properly spliced RNAs immediately 5' and 3', respectively, of the combined signature tag. The primer pair will amplify an approximate (25+56+24+23=) 128-base pair fragment from cDNA resulting from transcription of the unit.

The signature tag-containing cDNAs are amplified for 10 to 15 rounds of PCR amplification using Pwo polymerase (Roche), and using the above pair of primers. The amplification mixture is gel-purified to recover a 128 bp DNA representing the partially amplified probe population. Total yield of amplified cDNA is estimated at 100 nanograms (assuming 50 grams (packed cell volume) BMS cells at $2 \times 10^5$ cells per gram; efficiency of transient DNA delivery/expression=10%, average of 1000 transcripts/cell (non-induced), molecular weight of probe cDNA=60,000 grams/mol, and 12 rounds of PCR).

In vitro, dye-labeled transcripts are prepared from amplified signature DNA's essentially as described by Relogio (2002) Nucleic Acids Research 30:e51. Approx. 100 ng of template DNA is incubated with 2.0 units/ul of T7 RNA polymerase in a reaction mixture with 100 uM florescent-labeled CTP (either cyanine 5-CTP or cyanine-3-CTP, from NEN or Molecular Probes); 200 uM ATP, GTP, and TTP. The reaction mixture is digested with 10 U of RNAse-free DNAse I (Promega) to remove template DNA, and purified on a spin column.

Example 4

Readout of Tag Expression Levels Using Oligo Array

An oligonucleotide array is designed so as to include exact antisense complements to both left and right signature half-tags (28-mers), arranged either in tandem or mixed format on the slide or chip. For example, if the left and right tags have a complexity of 1024 tags each, a 2048-feature array would be created. Oligo arrays suitable for this task are manufactured by Agilent and others. Relogio et al. (2002, supra) describes a variety of oligo array methods and strategies.

Optionally, a set of mismatched oligos can be prepared, representing a 1 to 4-bp mismatch from each tag oligo. This is done by switching equal numbers of purine or pyrimidine bases.

The oligo array is probed with fluorescent-labeled tag-specific cRNA probe, prepared as above, representing several time points after co-cultivation, under conditions that preclude hybridization of mismatched probe. The array is read out using appropriate hardware and software for quantitating fluorescence in each array location.

Both left and right-half-tag array data are analyzed so as to identify any array locations in which signal increased significantly over time when compared to background (represented by the majority of cells). There should be an equal number of left and right tag array locations showing an increase in signal, since both classes were originally part of the same mRNA molecule which was induced. These array locations represent candidate signature tag combinations, which must next be decoded by PCR.

Example 5

PCR Rescue of Candidate Activators Using Signature Tag Oligos

A nested PCR approach is used to amplify up the candidate activator from the second, CaMV 35S Promoter-driven PTU, using as a template DNA from an aliquot of the original M4-STE-JT Agro library that was used for cocultivation. The oligo array identified a small number of half-tags that can be assumed to be associated with one or more activators, and since any given half-tag combination will be extremely rare, we can take advantage of the combined specificity of two half-tags via PCR. First, an oligonucleotide homologous to one half-tag is used in combination with a vector-specific oligo from the other end of the second PTU to amplify up a subfamily of clones containing that half-tag. The second tag is used in a nested manner to amplify up only the subset of amplified clones that contain the second half-tag.

Antisense strand PCR primers corresponding to candidate signature tags are synthesized (or drawn from a stock of the complete oligo population, prepared in advance). All possible combinations of half-tag oligos are used in a nested PCR reaction to amplify inserts, using Agro plasmid DNA prepared in Example 3, above, as a template, and a common 5' (sense strand) vector oligo from the Ubi intron or 5' UTR region of the PTU, as a third primer in both PCR reactions. To be sure of resolving all tag combinations, the number of PCR runs should be the square of the number of candidate tags identified. For example, if there were 4 candidates tags each from 5' and 3' arrays, a total of 4×4=16 PCR reactions would be run.

Alternatively, first strand cDNA prepared from oligo dT-primed cDNA synthesis (from RNA extracted from BMS suspensions in Example 3, above) can be used as template.

Aliquots of the resulting nested PCR reaction mixes are elecrophoresed on an agarose gel to determine which ones gave an amplified product. In the example above, only four of 16 combinations should yield a significant PCR product, representing left and right half-tags, respectively, from the same RNA transcript. Based on the infrequency of specific left-and-right tag combinations in the library, very few false positives will occur.

PCR inserts obtained above are cloned and sequenced (or sequenced directly) using primers directed towards the open reading frame from the Ubi intron region on one end and the PinII terminator region on the other.

Confirmation of Gene Activation

The promoter-activating activity of positive inserts is confirmed by cloning the insert obtained from PCR back into an *Agrobacterium* expression vector and repeating the cocultivation experiment, or by rescuing the positive clone from the original JT Agro library by colony hybridization.

Example 6

Screening a Library of JT *Agrobacterium* Vectors in a Cell Suspension Culture-Based HTP System All liquid handling and transfers are done with a multi-channel pipettor. When the system is scaled up, an automation machine, such as SciClone, Hamilton MPH96, Titertek, Matrix, etc, can be utilized.

On Day 1, 96 well plates are filled with 150 µl 557A+ Spectinomycin per well. If desired, Q-fill can be used to do this. Q-Bot picks up *Agrobacterium* colonies that contain JT Agro vectors from the target library, grown on Q-trays and transfers the colonies to the prepared 96-well plates. The colonies are cultured at 200 rpm overnight. For a library of 10,000 clones, it will take about 4–5 hrs for the Q-Bot to do the job (need about 104, 96-well or 26, 386-well plates).

The following day, a replicator is used to make duplicates of the *Agrobacterium* cultures in fresh 96-well plates containing 100 µl liquid 557A+AS+Spectinomycin medium in each well. When performing co-*Agrobacterium* delivery, the marker strain is added to each well at an $O.D._{550}=0.25$. The original set of plates is stored at 4° C. The new set is cultured at 200 rpm overnight. The new set is used as the *Agrobacterium* inocula to the BMS cells.

Prepare 96-well plates with 100 µl solid 562P medium at least one day in advance. BMS cells are prepared as in Example 3 on day 3. Aliquot 70 µl BMS cells into each well of the 96-well plates containing solid 562P medium. Use wide bore pipet tips to transfer the BMS cells. Transfer 10 µl of the *Agrobacterium* inocula to the BMS cells in corresponding order. Maintain the plate numbers and orientations for the *Agrobacterium* inocula and BMS plates. Co-cultivate the *Agrobacterium*-BMS at 140 rpm for 3 hours at 28° C. Remove all the liquid from each well using Flat MicroFlex tips with a narrow opening. Incubate the plates for one or two days at 28° C.

Detect a gain or loss of function of the reporter gene or change of expression levels of the U-tag signature tags. Identify which well shows the change and align the well with the *Agrobacterium* master plate for the corresponding *Agrobacterium* clone. Analyze and characterize the identified *Agrobacterium* clone. Repeat the experiments to confirm the results.

The principles exemplified in the Examples above can be used in a variety of other vector designs, including a dual PTU vector with 5' UTR signature tag instead of 3', or a single PTU vector with either 3' or 5' or split (5' and 3') signature tag. Vector construction, probing and clone rescue strategies are somewhat different in each case, but fundamentally they operate on the same ideas for clone identification and rescue. There may be advantages or disadvantages to each, depending on the application. The single PTU strategy is attractive because of the possibility of positive feedback between an activator and its promoter, leading potentially to very high levels of message. However, if a wide variety of clones are being screened, it is possible that the message stability from clone to clone will vary widely, adding to noise. If on the other hand a homogenous (but variable) population is being screened (such as mutated or recombined versions of the same gene), the single PTU method may be preferred. The choice of 5' or 3' location for the signature tag and intron depends on how well the promoter functions with additional sequence at one end or the other, determined in some cases empirically. Placing tags at both 3' and 5' ends simplifies PCR rescue somewhat, but also entails a more complex vector construction, since half-tag libraries are separate and need to be added sequentially in two large-scale ligation/cloning steps.

All publications, patents, and patent applications mentioned in the specification are indicative of the level of those skilled in the art to which this invention pertains. All publications, patents, and patent applications are herein incorporated by reference to the same extent as if each individual publication or patent application was specifically and individually indicated to be incorporated by reference.

Although the foregoing invention has been described in some detail by way of illustration and example for purposes That which is claimed:

1. A method of identifying a nucleotide sequence that modulates the activity of a transcriptional regulatory region, comprising:
   a) incorporating into a host cell population a generated library of plasmids wherein the generated library is a collection of plasmids, wherein the library of plasmids comprises multiple non-redundant U-tags, each plasmid having one or more non-redundant U-tags, each U-tag conferring an identifying marker on each plasmid in the library, and each plasmid in the generated library comprises a first DNA construct and a second DNA construct, wherein;
      i) the first DNA construct comprises a transcriptional regulatory region, a reporter sequence, and an mRNA stabilizing sequence; and,
      ii) the first DNA construct further comprises one or more U-tags inserted into one or more locations selected from the group of locations consisting of a 3' UTR of the transcriptional regulatory region, a 5' UTR of the transcriptional regulatory region, a coding region of the reporter sequence, and one or more intron sequences occurring within the first DNA construct; and,
      iii) the second DNA construct comprises a promoter active in a host cell of the host cell population, wherein the promoter is operably linked to a nucleotide sequence of interest; and
   b) screening for an alteration in the expression levels of each U-tag; and,
   c) identifying the nucleotide sequence of interest based on U-tag identity.

2. The method of claim 1 further comprising isolating from the library at least one plasmid having one or more U-tags, wherein the expression level of the one or more U-tags is altered.

3. The method of claim 2 wherein the isolating comprises PCR.

4. The method of claim 2 wherein the isolating comprises hybridization.

5. The method of claim 1 wherein the nucleotide sequence of interest comprises a nucleic acid sequence selected from the group consisting of a cDNA, a genomic DNA, or a mutagenized nucleic acid sequence.

6. The method of claim 1 wherein the first DNA construct is located 5' to the second DNA construct.

7. The method of claim 1 wherein the first DNA construct is located 3' to the second DNA construct.

8. The method of claim 1 wherein the first and second DNA constructs are contiguous.

9. The method of claim 1 wherein the first and second DNA constructs are not contiguous.

10. The method of claim 1 wherein the one or more non-redundant U-tags are located 5' to the reporter sequence.

11. The method of claim 1 wherein the one or more non-redundant U-tags are located 3' to the reporter sequence.

12. The method of claim 1 wherein the one or more non-redundant U-tags are located 5' and 3' to the reporter sequence.

13. The method of claim 1 wherein the one or more non-redundant U-tags are located in the coding region of the reporter sequence.

14. The method of claim 1 wherein the one or more non-redundant U-tags are located within the one or more intron sequences occurring within the transcriptional regulatory region.

15. The method of claim 1 wherein the screening for an alteration in the expression levels of each U-tag comprises hybridization to a complementary U-tag array.

16. The method or claim 1 wherein the screening for an alteration in the expression levels of each U-tag comprises sequence probe concatamer methods.

17. The method of claim 1 wherein the screening For an alteration in the expression levels of each U-tag comprises a solid phase capture system.

18. The method of claim 1 wherein the alteration in the expression levels of each U-tag comprises an increase in U-tag expression levels.

19. The method of claim 1 wherein the alteration in the expression levels of each U-tag comprises a decrease in U-tag expression levels.

20. The method of claim 1 wherein the transcriptional regulatory region of the first DNA construct regulates expression of a sequence involved in a physiological pathway of interest.

21. The method of claim 20 wherein the physiological pathway of interest is a pathogen resistance pathway.

22. The method of claim 20 wherein the physiological pathway of interest is a tissue developmental pathway.

23. The method of claim 20 wherein the physiological pathway of interest is a metabolic pathway.

24. The method of claim 20 wherein the physiological pathway of interest is an apoptotic pathway.

25. The method of claim 1 wherein the host cells are plant cells.

26. The method of claim 25 wherein the plant cells are dicotyledonous cells.

27. The method of claim 25 wherein the plant cells are monocotyledonous cells.

28. The method of claim 27 wherein the monocotyledonous cells are Black Mexican Sweet maize (BMS) cells.

29. The method of claim 25 wherein the plant cells are selected from the group consisting of maize, wheat, sorghum, rice, barley, soybean, alfalfa, sunflower, *Brassica*, and tomato.

30. The method of claim 1 wherein the host cells are mammalian cells.

31. The method of claim 1 wherein the nucleotide sequence of interest encodes a polypeptide that directly modulates the activity of the transcriptional regulatory region.

32. The method of claim 2 wherein the nucleotide sequence of interest encodes a polypeptide that indirectly modulates the activity of the transcriptional regulatory region.

33. A method for identifying a transcriptional regulatory region of interest that is modulated by an agent, comprising:
   a) incorporating into a host cell population a generated library of plasmids wherein the generated library is a collection of plasmids, wherein the library of plasmids comprises multiple non-redundant U-tags, each plasmid having one or more non-redundant U-tags, each U-tag conferring an identifying marker on each plasmid in the library, and each plasmid in the generated library comprises a first DNA construct, wherein
      i) the first DNA construct comprises the transcriptional regulatory region of interest, a reporter sequence, and an mRNA stabilizing sequence, and;

ii) the first DNA construct further comprises one or more U-tags inserted into one or more locations selected from the group of locations consisting of a 3' UTR of the transcriptional regulatory region, a 5' UTR of the transcriptional regulatory region, a coding region or the reporter sequence, and one or more intron sequences occurring within the first DNA construct; and b) contacting the host cell population with an agent; and c) screening for an alteration in the expression levels of each U-tag.

34. The method of claim 33 wherein the agent is selected from the group consisting of a pathogen, a polypeptide, a nucleotide sequence, and a small molecule.

35. The method of claim 34, wherein the plasmid in the generated library further comprises a second DNA construct operably linked to a promoter active in a host cell of the host cell population.

36. The method of claim 33 further comprising isolating from the library at least one plasmid having one or more U-tags, wherein the expression level of one or more of the U-tags is altered.

37. The method of claim 36 wherein the method of isolation comprises PCR.

38. The method of claim 36 wherein the method of isolation comprises hybridization.

39. The method of claim 35 wherein the first DNA construct is located 5' to the second DNA construct.

40. The method of claim 35 wherein the first DNA construct is located 3' to the second DNA construct.

41. The method of claim 35 wherein the first and the second DNA constructs are contiguous.

42. The method of claim 35 wherein the first and the second DNA constructs are not contiguous.

43. The method of claim 33 wherein the one or more U-tags are located 5' to the reporter sequence.

44. The method of claim 33 wherein the one or more U-tags are located 3' to the reporter sequence.

45. The method of claim 33 wherein the one or more U-tags are located 5' and 3' to the reporter sequence.

46. The method of claim 33 wherein the one or more U-tags are located in the coding region of the reporter sequence.

47. The method of claim 33 wherein the one or more U-tags are located within the one or more intron sequences occurring within the transcriptional regulatory region.

48. The method or claim 33 wherein screening for an alteration in the expression levels of each U-tag comprises hybridization to a complementary U-tag array.

49. The method of claim 33 wherein screening for an alteration in the expression levels of each U-tag comprises a sequence probe concatamer method.

50. The method of claim 33 wherein screening for an alteration in the expression levels of each U-tag comprises a solid phase capture system.

51. The method of claim 33 wherein the alteration in the expression levels of each U-tag comprises an increase in U-tag expression levels.

52. The method of claim 33 wherein the alteration in the expression levels of each U-tag comprises a decrease in U-tag expression levels.

53. The method of claim 33 wherein the agent regulates expression of the transcriptional regulatory region sequence involved in a physiological pathway of interest.

54. The method of claim 53 wherein the physiological pathway or interest is a pathogen resistance pathway.

55. The method of claim 53 wherein the physiological pathway of interest is a tissue developmental pathway.

56. The method of claim 53 wherein the physiological pathway of interest is a metabolic pathway.

57. The method of claim 53 wherein the physiological pathway or interest is an apoptotic pathway.

58. The method of claim 33 wherein the host cells are plant cells.

59. The method of claim 58 wherein the plant cells are dicotyledonous cells.

60. The method of claim 58 wherein the plant cells are monocotyledonous cells.

61. The method of claim 60 wherein the monocotyledonous cells are Black Mexican Sweet maize (BMS) cells.

62. The method of claim 58 wherein the plant cells are selected from the group consisting of maize, wheat, sorghum, rice, barley, soybean, alfalfa, sunflower, *Brassica*, and tomato.

63. The method of claim 33 wherein the host cells are mammalian cells.

64. A method of identifying a nucleotide sequence of interest that modulates the activity of a transcriptional regulatory region, comprising:

a) incorporating into a host cell population a generated library of plasmids wherein the generated library is a collection of plasmids, wherein the library of plasmids comprises multiple non-redundant U-tags, each plasmid having one or more non-redundant U-tags, each U-tag conferring an identifying marker on each plasmid in the library, and each plasmid in the generated library comprises a first DNA construct wherein i) the first DNA construct comprises a transcriptional regulatory region, a nucleotide sequence of interest, and an mRNA stabilizing sequence; and ii) the first DNA construct further comprises one or more U-tags inserted into one or more locations selected from the group of locations consisting of a 3' UTR of the transcriptional regulatory region, a 5' UTR of the transcriptional regulatory region, a coding region of the reporter sequence, and one or more intron sequences occurring within the first DNA construct; and b) screening for an alteration in the expression level of each U-tag and;

c) identifying the sequence of interest based on U-tag identity.

65. The method of claim 64 further comprising isolating from the library at least one plasmid having one or more U-tags, wherein the expression level of the U-tag is altered.

66. The method of claim 64 wherein the alteration in the expression levels of each U-tag comprises an increase in U-tag expression levels.

67. A method for identifying a nucleotide sequence of interest that modulates cell death, comprising:

a) incorporating into a host cell a plasmid having at least a first DNA construct and a second DNA construct, wherein:

i) the first DNA construct comprises a transcriptional regulatory region, a reporter sequence, and an mRNA stabilizing sequence; and, ii) the first DNA construct further comprises one or more U-tags inserted into one or more locations selected from the group of locations consisting of a 3' UTR of the transcriptional regulatory region, a 5' UTR of the transcriptional regulatory region, a coding region of the reporter sequence, and one or more intron sequences occurring within the first DNA construct; and,
b) the second DNA construct comprises a promoter active in the host cell operably linked to the nucleotide sequence of interest; and c) screening for a loss in the expression level of the U-tag; and
d) identifying the sequence of interest based on U-tag identity.

* * * * *

UNITED STATES PATENT AND TRADEMARK OFFICE
CERTIFICATE OF CORRECTION

| | |
|---|---|
| PATENT NO. | : 7,026,123 B1 |
| APPLICATION NO. | : 10/229608 |
| DATED | : April 11, 2006 |
| INVENTOR(S) | : Duvick |

It is certified that error appears in the above-identified patent and that said Letters Patent is hereby corrected as shown below:

Column 31,

Line 6, "region or" should read –region of".

Signed and Sealed this

Eighth Day of August, 2006

JON W. DUDAS
*Director of the United States Patent and Trademark Office*